United States Patent [19]

Wu et al.

[11] Patent Number: 6,025,293

[45] Date of Patent: Feb. 15, 2000

[54] HYDROCARBON CONVERSION CATALYST COMPOSITION AND PROCESSES THEREFOR AND THEREWITH

[75] Inventors: An-hsiang Wu; Ralph J. Melton, both of Bartlesville; Charles A. Drake, Nowata, all of Okla.

[73] Assignee: Phillips Petroleum Company, Bartlesville, Okla.

[21] Appl. No.: 09/264,934

[22] Filed: Mar. 9, 1999

Related U.S. Application Data

[62] Division of application No. 08/907,194, Aug. 6, 1997, Pat. No. 5,929,295.

[51] Int. Cl.[7] .............................. B01J 29/04; B01J 29/06; B01J 21/00; B01J 21/16; C01G 35/06

[52] U.S. Cl. .............................. 502/60; 502/64; 502/66; 502/74; 502/80; 502/81; 208/137

[58] Field of Search .................................. 502/60, 64, 66, 502/74, 80, 81; 208/137

[56] References Cited

U.S. PATENT DOCUMENTS

| | | | |
|---|---|---|---|
| 3,671,602 | 6/1972 | Inoue et al. | 260/672 T |
| 4,267,072 | 5/1981 | Vasalos | 252/455 Z |
| 4,367,165 | 1/1983 | Asaoka et al. | 252/457 |
| 4,739,940 | 4/1988 | Dufresne et al. | 502/66 |
| 4,780,436 | 10/1988 | Raatz et al. | 502/66 |
| 4,983,274 | 1/1991 | Chen et al. | 208/111 |
| 5,506,182 | 4/1996 | Yamagishi et al. | 502/66 |
| 5,689,026 | 11/1997 | Wu et al. | 585/475 |
| 5,698,757 | 12/1997 | Wu et al. | 585/488 |
| 5,804,059 | 9/1998 | Wu et al. | 208/135 |
| 5,807,799 | 9/1998 | Drake et al. | 502/67 |
| 5,827,422 | 10/1998 | Drake et al. | 208/135 |
| 5,866,742 | 2/1999 | Wu et al. | 585/475 |
| 5,866,744 | 2/1999 | Wu et al. | 585/486 |
| 5,883,033 | 3/1999 | Drake et al. | 502/68 |
| 5,905,051 | 5/1999 | Wu et al. | 502/60 |

*Primary Examiner*—Gary P. Straub
*Assistant Examiner*—Cam N. Nguyen

[57] ABSTRACT

A catalyst composition, a process for producing the composition and a hydrocarbon conversion process for converting a $C_9+$ aromatic compound to a $C_6$ to $C_8$ aromatic hydrocarbon such as a xylene are disclosed. The composition comprises an acid-treated zeolite having impregnated thereon a metal or metal oxide. The composition can be produced by incorporating the metal or metal oxide into the zeolite. The hydrocarbon conversion process comprises contacting a fluid which comprises a $C_9+$ aromatic compound with the catalyst composition under a condition sufficient to effect the conversion of a $C_9+$ aromatic compound to a $C_6$ to $C_8$ aromatic hydrocarbon.

7 Claims, No Drawings

HYDROCARBON CONVERSION CATALYST COMPOSITION AND PROCESSES THEREFOR AND THEREWITH

This application is a division of application Ser. No. 08/907,194 filed on Aug. 6, 1997, now U.S. Pat. No. 5,929,295.

FIELD OF THE INVENTION

This invention relates to a catalyst composition useful for converting a $C_9+$ aromatic compound to a $C_6$ to $C_8$ aromatic hydrocarbon, to a process for producing the composition and to a process for using the composition in a hydrodealkylation process.

BACKGROUND OF THE INVENTION

It is well known to those skilled in the art that aromatic hydrocarbons are a class of very important industrial chemicals which find a variety of uses in petrochemical industry. Recent efforts to convert gasoline to more valuable petrochemical products have therefore focused on the aromatization of gasoline to aromatic hydrocarbons by catalytic cracking in the presence of a catalyst. The aromatic hydrocarbons produced by the aromatization process include $C_6$ to $C_8$ hydrocarbons such as benzene, toluene and xylenes (hereinafter collectively referred to as BTX) which can be useful feedstocks for producing various organic compounds and polymers. However, heavier, less useful aromatic compounds are also produced during the aromatization process. It is, therefore, highly desirable to convert these compounds to the more useful BTX.

Though a number of catalysts have been used in a hydrodealkylation or transalkylation process, the conversion of a $C_9+$ aromatic compound and the selectivity to BTX are generally not as high as one skilled in the art would desire. Furthermore, a catalyst used in the hydrodealkylation or transalkylation of these heavier aromatic compounds is generally deactivated in a rather short period because of depositions of carbonaceous material such as, for example, coke on the surface of the catalyst.

Accordingly, there is an ever-increasing need to develop a catalyst and a process for converting these heavier and less useful aromatic compounds (mainly trimethyl- and tetramethylbenzenes) to the more valuable BTX hydrocarbons while simultaneously suppressing the coke formation. Such development would also be a significant contribution to the art and to the economy.

SUMMARY OF THE INVENTION

An object of this invention is to provide a catalyst composition which can be used to convert a $C_9+$ aromatic compound to a $C_6$ to $C_8$ aromatic hydrocarbon. Also an object of this invention is to provide a process for producing the catalyst composition. Another object of this invention is to provide a process which can employ the catalyst composition to convert $C_9+$ aromatic compounds to $C_6$ to $C_8$ aromatic compounds. An advantage of the catalyst composition is that it decreases coke deposits thereon and exhibits high transalkylation activity, satisfactory yield of xylenes and BTX and good stability. Other objects and advantages will become more apparent as this invention is more fully disclosed hereinbelow.

According to a first embodiment of the present invention, a composition which can be used as a catalyst for converting a $C_9+$ aromatic compound to a $C_6$ to $C_8$ aromatic hydrocarbon is provided. The composition can comprise an acid-treated zeolite having incorporated therein an activity promoter.

According to a second embodiment of the invention, a process for producing a composition which can be used as catalyst in a hydrocarbon conversion is provided. The process can comprise (1) optionally calcining a zeolite to produce a calcined zeolite; (2) contacting a zeolite or a calcined zeolite with an acid under a condition sufficient to produce an acid-treated zeolite; (3) contacting the acid-treated zeolite with an activity promoter precursor selected from the group consisting of silicon compounds, phosphorus compounds, boron compounds, magnesium compounds, tin compounds, titanium compounds, zirconium compounds, molybdenum compounds, germanium compounds, indium compounds, lanthanum compounds, cesium compounds, and combinations of two or more thereof under a condition sufficient to incorporate the activity promoter into the zeolite to form a modified zeolite; and (4) calcining the modified zeolite.

According to a third embodiment of the present invention, a process which can be used for converting a $C_9+$ aromatic compound to a $C_6$ to $C_8$ aromatics compound is provided which comprises, consists essentially of, or consists of, contacting a fluid which comprises a $C_9+$ aromatic compound, optionally in the presence of an inert fluid such as a hydrogen-containing fluid, with a catalyst composition, which is the same as disclosed above in the first embodiment of the invention, under a condition effective to convert a $C_9+$ aromatic compound to an aromatic hydrocarbon containing 6 to 8 carbon atoms per molecule.

DETAILED DESCRIPTION OF THE INVENTION

According to the first embodiment of the invention, a composition which can be used as catalyst in a transalkylation or hydrodealkylation process for converting a $C_9+$ aromatic compound to a $C_6$ to $C_8$ aromatic hydrocarbon is provided. The composition comprises, consists essentially of, or consists of, a zeolite having incorporated therein, preferably impregnated thereon, an activity promoter selected from the group consisting of silicon, phosphorus, boron, magnesium, tin, titanium, zirconium, molybdenum, germanium, indium, lanthanum, cesium, any oxide thereof, and combinations of two or more thereof wherein the activity promoter is present in the composition in a coke-suppressing amount, or an activity-enhancing amount to improve the conversion of a $C_9+$ aromatic compound, when the composition is used in a transalkylation process.

According to the first embodiment of the invention, the weight ratio of the activity promoter to the acid-treated zeolite can be any ratio so long as the ratio can enhance or improve the conversion of a $C_9+$ aromatic compound or suppress or reduce the formation or deposition of coke on a zeolite catalyst during the transalkylation process for converting a $C_9+$ aromatic compound to a $C_6$ to $C_8$ aromatic hydrocarbon. Generally, the ratio can be in the range of from about 0.0001:1 to about 1:1, preferably about 0.0005:1 to about 1:1, more preferably about 0.00 1:1 to about 0.8: 1 and most preferably from 0.005:1 to 0.5:1 for effective hydrocarbon conversion and coke reduction or suppression. Alternatively, the activity promoter can be present in the catalyst composition in the range of from about 0.01 to about 50, preferably about 0.05 to about 50, more preferably about 0.1 to about 45, and most preferably 0.5 to 33 grams per 100 grams of the catalyst composition. The term "acid-treated zeolite" refers to a zeolite which has been contacted with an acid, as described in the second embodiment of the invention, before the zeolite is incorporated with an activity promoter.

If a combination of two or more activity promoters is employed, the atomic ratio of one promoter to other promoter(s) can be in the range of about 0.01:1 to about 10:1, preferably about 0.1:1 to about 8:1, more preferably about 0.5:1 to about 5:1, and most preferably 1:1 to 3:1. The presently preferred composition is an acid-treated beta zeolite having impregnated thereon molybdenum or molybdenum oxide.

According to the present invention, any activity promoter that, as compared to use of a zeolite only, can effect the increase in the conversion of a $C_9+$ aromatic compound to a $C_6$–$C_8$ aromatic hydrocarbon or reduction of coke deposition on the zeolite during the conversion of a $C_9+$ aromatic compound to a $C_6$ to $C_8$ aromatic hydrocarbon, can be employed. Presently it is preferred that the activity promoter is selected from the group consisting of silicon, phosphorus, boron, magnesium, tin, titanium, zirconium, molybdenum, germanium, indium, lanthanum, cesium, any oxides thereof, and combinations of two or more thereof. The presently most preferred activity promoter is molybdenum or molybdenum oxide.

The composition can also be characterized by having the following physical characteristics: a micropore surface area, as determined by the BET method using nitrogen, in the range of from about 50 to about 1,000, preferably 50 to 500 $m^2/g$; a micropore pore volume in the range of from about 0.1 to about 2.0, preferably about 0.1 to about 1.0 ml/g; an average micropore pore diameter in the range of from about 0.1 to about 500, preferably about 1 to about 200 Å; and a porosity of more than about 20%.

Any commercially available zeolites can be employed as a starting material of the process of the second embodiment of the invention. Examples of suitable zeolites include, but are not limited to, those disclosed in Kirk-Othmer Encyclopedia of Chemical Technology, third edition, volume 15 (John Wiley & Sons, New York, 1991). The presently preferred zeolite, as disclosed above, is a beta zeolite.

Any methods known to one skilled in the art for incorporating a compound or a portion thereof into a zeolite such as, for example, impregnation, ion exchange, or extrusion can be employed for producing the composition of the present invention. However, it is presently preferred the composition be produced by the process disclosed in the second embodiment of the invention.

According to the second embodiment of the invention, a zeolite, preferably a beta zeolite, can be optionally contacted with one or more suitable binders in a liquid, preferably aqueous medium, to form a zeolite-binder mixture. Any binders known to one skilled in the art for use with a zeolite are suitable for use herein. Examples of suitable binder include, but are not limited to, clays such as for example, kaolinite, halloysite, vermiculite, chlorite, attapulgite, smectite, montmorillonite, illite, saconite, sepiolite, palygorskite, and combinations of two or more thereof; diatomaceous earth; aluminas such as for example α-alumina and γ-alumina; silicas; alumina-silica; aluminum phosphate; aluminum chlorohydrate; and combinations of two or more thereof. Because these binders are well known to one skilled in the art, description of which is omitted herein. The weight ratio of a zeolite to a binder can be in a wide range and generally in the range of from about 200:1 to about 0.1:1, preferably 20:1 to 0.1:20.

The zeolite and the binder can be well mixed by any means known to one skilled in the art such as stirring, blending, kneading, or extrusion, following which the zeolite-binder mixture can be dried in air at a temperature in the range of from about 20 to about 200° C., preferably about 25 to about 175° C., and most preferably 25 to 150° C. for about 0.5 to about 50 hours, preferably about 1 to about 30 hours, and most preferably 1 to 20 hours, preferably under atmospheric pressure. Thereafter, the dried, zeolite-binder mixture can be further calcined, if desired, in air at a temperature in the range of from about 300 to 1000° C., preferably about 350 to about 750° C., and most preferably 450 to 650° C. for about 1 to about 30 hours to prepare a calcined zeolite-binder. If a binder is not desired, a zeolite can also be calcined under similar conditions to remove any contaminants, if present.

A zeolite, a calcined zeolite, or a calcined zeolite-binder can be treated with a compound containing an exchangeable ammonium ion to prepare an ammonium-exchanged zeolite. Whether a zeolite is calcined or contains a binder, the process or treatment in the second embodiment is the same for each. For the interest of brevity, only a zeolite is described hereinbelow. Examples of suitable ammonium-containing compounds include, but are not limited to, ammonium sulfate, ammonium chloride, ammonium nitrate, ammonium bromide, ammonium fluoride, and combinations of any two or more thereof. Treatment of the zeolite replaces the original ions such as, for example, alkali or alkaline earth metal ions of the zeolite with predominantly ammonium ions. Techniques for such treatment are well known to one skilled in the art such as, for example, ion exchange with the original ions. For example, a zeolite can be contacted with a solution containing a salt of the desired replacing ion or ions.

Generally, a zeolite can be suspended in an aqueous solution of an ammonium compound. The concentration of the zeolite in the aqueous solution can be in the range of from about 0.01 to about 200, preferably about 0.1 to about 150, more preferably about 1 to about 100, and most preferably 5 to 75 grams per liter. The amount of the ammonium compound required depends on the amount of the original ion(s) to be exchanged. Upon the preparation of the solution, the solution can be subject to a temperature in the range of from about 30° C. to about 200° C., preferably about 40° C. to about 150° C., and most preferably 50° C. to 125° C. for about 1 to about 100 hours, preferably about 1 to about 50 hours, and most preferably 2 to 25 hours depending on desired degrees of ion exchange. The treatment can be carried out under a pressure in the range of from about 1 to about 10 atmospheres (atm), preferably about 1 atm or any pressure that can maintain the required temperature. Thereafter, the treated zeolite can be washed with running water for 1 to about 60 minutes followed by drying and calcining to produce calcined zeolite. The drying and calcining processes can be carried out substantially the same as those disclosed above for the preparation of a calcined zeolite or zeolite-binder.

Generally, the ammonium-exchanged zeolite becomes hydrogen exchanged upon calcination or high temperature treatment such that a predominant proportion of its exchangeable cations are hydrogen ions. The above-described ion exchanges of exchangeable ions in a zeolite is well known to one skilled in the art. See, for example, U.S. Pat. No. 5,516,956, disclosure of which is incorporated herein by reference. Because the ion exchange procedure is well known, the description of which is omitted herein for the interest of brevity.

According to the second embodiment of the invention, a zeolite in a desired ionic form, regardless whether calcined or containing a binder, can be optionally contacted with steam under a condition sufficient to effect the formation of steamed zeolite. Generally the steam temperature can be in the range of from about 120° C. to about 1500° C., preferably about 200° C. to about 1000° C., more preferably 250° C. to 800° C., and most preferably 350 to 625 ° C. The treatment can be carried out under a pressure that can maintain or accommodate the steam temperature in the range of from about atmospheric pressure to about 2,000, preferably to about 1,500, and most preferably to 1000 psig.

According to the second embodiment of the invention a zeolite, whether it has been steamed or not, also can be treated with an acid. Generally, any organic acids, inorganic acids, or combinations of any two or more thereof can be used in the process of the present invention so long as the acid can reduce the aluminum content in the zeolite. The acid can also be a diluted aqueous acid solution. Examples of suitable acids include, but are not limited to oxalic acid, citric acid, sulfuric acid, hydrochloric acid, nitric acid, phosphoric acid, formic acid, acetic acid, trifluoroacetic acid, trichloroacetic acid, p-toluenesulfonic acid, methanesulfonic acid, partially or fully neutralized acids wherein one or more protons have been replaced with, for example, a metal (preferably an alkali metal) or ammonium ion, and combinations of any two or more thereof. Examples of partially or fully neutralized acids include, but are not limited to, sodium bisulfate, sodium dihydrogen phosphate, potassium hydrogen tartarate, ammonium sulfate, ammonium chloride, ammonium nitrate, and combinations of two or more thereof. The presently preferred acid is oxalic acid.

Any methods known to one skilled in the art for treating a solid catalyst with an acid can be used in the acid treatment of the present invention. Generally, a zeolite material can be suspended in an acid solution. The concentration of the zeolite in the acid solution can be in the range of from about 0.01 to about 500, preferably about 0.1 to about 400, more preferably about 1 to about 350, and most preferably 5 to 300 grams per liter. The amount of acid required is the amount that can maintain the solution in acidic pH during the treatment. Generally the weight ratio of the zeolite to acid can be in the range of from about 0.001:1 to about 100:1 depending on the type of acid employed. Preferably the initial pH of the acid solution containing a zeolite is adjusted to lower than about 7, and preferably lower than about 6. Upon the pH adjustment of the solution, the solution can be subjected to a treatment at a temperature in the range of from about 30° C. to about 200° C., preferably about 35° C. to about 150° C., and most preferably 40° C. to 120° C. for about 10 minutes to about 30 hours, preferably about 20 minutes to about 25 hours, and most preferably 30 minutes to 20 hours. The treatment can be carried out under a pressure in the range of from about 1 to about 10 atmospheres (atm), preferably about 1 atm so long as the desired temperature can be maintained. Thereafter, the acid-treated zeolite material can be washed with running water for 1 to about 60 minutes followed by drying, at about 50 to about 1000, preferably about 75 to about 750, and most preferably 100 to 650° C. for about 0.5 to about 15, preferably about 1 to about 12, and most preferably 1 to 10 hours, to produce an acid-treated zeolite. Any drying method known to one skilled in the art such as, for example, air drying, heat drying, spray drying, fluidized bed drying, or combinations of two or more thereof can be used.

The dried, acid-treated zeolite can also be further washed, if desired, with a mild acid solution such as, for example, ammonium nitrate which is capable of maintaining the pH of the wash solution in acidic range. The volume of the acid generally can be the same volume as the acid for reducing the aluminum content in a zeolite. The mild acid treatment can be carried out under substantially the same conditions disclosed in the acid treatment for reducing aluminum content in a zeolite. Thereafter, the resulting solid can be washed and dried as disclosed above.

The dried, acid-treated zeolite, whether it has been further washed with a mild acid or not, can be calcined, if desired, under a condition known to those skilled in the art. Generally such a condition can include a temperature in the range of from about 250 to about 1,000, preferably about 350 to about 750, and most preferably 450 to 650° C. and a pressure in the range of from about 0.5 to about 50, preferably about 0.5 to about 30, and most preferably 0.5 to 10 atmospheres (atm) for about 1 to about 30 hours, preferably about 2 to about 20 hours, and most preferably 3 to 15 hours.

Thereafter, the acid-treated zeolite, whether it has been calcined or not, can be incorporated therein, or preferably impregnated thereon an activity promoter precursor. According to the second embodiment of the present invention, any activity promoter precursor which can be converted to an activity promoter, as disclosed in the first embodiment of the invention, that, as compared to use of a zeolite or acid-treated zeolite only, can effect the improvement of conversion of a $C_9+$ aromatic compound to BTX or xylene or the reduction of coke in a transalkylation process, can be employed. Presently it is preferred that an activity promoter precursor be selected from the group consisting of molybdenum compounds, lanthanum compounds, phosphorus compounds, boron compounds, magnesium compounds, tin compounds, titanium compounds, zirconium compounds, germanium compounds, indium compounds, cesium compounds, and combinations of two or more thereof.

Generally any lanthanum compounds which, when incorporated or impregnated into a zeolite are effective to enhance the conversion of a $C_9+$ aromatic compound, can be used in the present invention. Examples of suitable lanthanum compounds include, but are not limited to, lanthanum acetate, lanthanum carbonate, lanthanum octanoate, lanthanum fluoride, lanthanum chloride, lanthanum bromide, lanthanum iodide, lanthanum nitrate, lanthanum perchlorate, lanthanum sulfate, lanthanum titanate, and combinations of two or more thereof.

Similarly, any molybdenum compounds which, when incorporated or impregnated into a zeolite are effective to enhance the conversion of a $C_9+$ aromatic compound can be used in the present invention. Suitable molybdenum compounds include, but are not limited to, molybdenum (II) chloride, molybdenum(III) chloride, molybdenum(II) acetate, molybdenum(IV) chloride, molybdenum(V) chloride, molybdenum(VI) fluoride, molybdenum hexacarbonyl, molybdenum sulfide, sodium molybdates, potassium molybdates, molybdenum(VI) oxychloride, molybdenum(IV) sulfide, ammonium tetrathiomolybdate, ammonium molybdate, ammonium dimolybdate, ammonium heptamolybdate(VI), and combinations of two or more thereof.

Examples of the other activity promoters can be found in applicants' copending application Ser. No. 08/705,926 in which the term "acid site modifier" instead of activity promoter is used therein, the disclosure of which is herein incorporated by reference.

Generally, a zeolite, calcined zeolite, zeolite-binder, calcined zeolite-binder or acid-treated zeolite, can be combined with such activity promoter precursor in any suitable weight ratios which would result in the weight ratios of an activity promoter to a zeolite disclosed in the first embodiment of the invention. Presently it is preferred that such combination be carried out in a suitable liquid, preferably an aqueous medium, to form an incipient wetness zeolite-precursor mixture or a modified zeolite.

The zeolite and the precursor are well mixed. In the next step of the process, the modified zeolite is subjected to calcination under a condition that can include a temperature in the range of from about 300° C. to about 1000° C., preferably about 350° C. to about 750° C., and most preferably 400° C. to 650° C. under a pressure that can accommodate the temperatures and is generally in the range of from about 1 to about 10, preferably about 1, atmospheres for a period in the range of from about 1 to about 30, preferably about 1 to about 20, and most preferably 1 to 15 hours. Upon completion of incorporating or impregnating the activity promoter into the zeolite by calcination, a promoted zeolite is formed.

The composition of the invention then can be, if desired, pretreated with a reducing agent before being used in a hydrodealkylation or a transalkylation process. The presently preferred reducing agent is a hydrogen-containing fluid which comprises molecular hydrogen ($H_2$) in the range of from 1 to about 100, preferably about 5 to about 100, and most preferably 10 to 100 volume %. The reduction can be carried out at a temperature, in the range of from about 250° C. to about 800° C. for about 0.1 to about 10 hours preferably about 300° C. to about 700° C. for about 0.5 to about 7 hours, and most preferably 350° C. to 650° C. for 1 to 5 hours.

According to the third embodiment of the present invention, a process comprises, consists essentially of, or consists of contacting a fluid stream with a catalyst composition, optionally in the presence of an inert gas, preferably a hydrogen-containing fluid, under a condition sufficient to enhance or effect the conversion of a hydrocarbon to a mixture rich in $C_6$ to $C_8$ aromatic hydrocarbons wherein said fluid stream comprises a hydrocarbon or hydrocarbon mixture which can comprise $C_9+$ aromatic compounds, paraffins, olefins, naphthenes. The catalyst composition is the same as that disclosed in the first embodiment of the invention which can be prepared by the second embodiment of the invention.

The term "fluid" is used herein to denote gas, liquid, vapor, or combinations thereof. The term "increase, improve, or enhance" refers to increased BTX in the product employing the catalyst composition as compared to employing an untreated zeolite. Examples of a hydrocarbon include, but are not limited to, butane, isobutanes, pentane, isopentanes, hexane, isohexanes, cyclohexane, methylcyclohexane, heptane, isoheptanes, octane, isooctanes, nonanes, decanes, undecanes, dodecanes, tridecanes, tetradecanes, pentadecanes, hexadecanes, butenes, isobutene, pentenes, hexenes, 1,2,3-trimethylbenzene, 1,2,4-trimethylbenzene, 1,3,5-trimethylbenzene, 1,2,3,4-tetramethylbenzene, 1,2,3,5-tetramethylbenzene, 1,2,4,5-tetramethylbenzene, n-propylbenzene, 3-ethyltoluene, 4-ethyltoluene, 3-n-propyltoluene, 4-n-propyltoluene, 1,3-diethylbenzene, naphthalenes, and combinations of any two or more thereof. In some feed fluids, such as, for example, gasoline can comprise some benzene, toluene, ethylbenzene, and xylenes.

Any fluid which contains a $C_9+$ aromatic compound can be used as the feed for the process of this invention.

Generally, the fluid feed stream can also contain olefins, naphthenes (cycloalkanes), or some aromatic compounds. Examples of suitable, available fluid feeds include, but are not limited to, gasolines from catalytic oil cracking processes, pyrolysis gasolines from thermal cracking of saturated hydrocarbons, naphthas, gas oils, reformates, and combinations of any two or more thereof. The origin of this fluid feed is not critical. Though particular composition of a feed is not critical, a preferred fluid feed is derived from gasolines which generally contain more paraffins (alkanes) than combined content of olefins, cycloalkanes, and aromatic compounds.

Any fluid which contains a $C_9$ + aromatic compound as disclosed above can also be used as the feed for the process of this invention. A $C_9+$ aromatic compound can have the formula of $R'_q Ar$ wherein each R' is a hydrocarbyl radical having 1 to about 15 carbon atoms and is independently selected from the group consisting of alkyl radicals, aryl radicals, alkaryl radicals, aralkyl radicals, alkenyl radicals, and combinations of any two or more thereof, q is a whole number from 1 to 5, and Ar is an aryl or arylene group. The origin of the $C_9+$ aromatic compounds feed is not critical. However, a preferred fluid feed is a $C_9+$ aromatic compound derived from the heavies fraction of a product from a paraffin, in particular gasoline, aromatization reaction. Generally, this heavies fraction contains primarily trimethylbenzenes such as 1,2,3-trimethylbenzene, 1,2,4-trimethylbenzene, and 1,3,5-trimethylbenzene; tetramethylbenzenes such as 1,2,3,4-tetramethylbenzene, 1,2,3,5-tetramethylbenzene and 1,2,4,5-tetramethylbenzene; and naphthalenes. Additionally, n-propylbenzene, 3-ethyltoluene, 4-ethyltoluene, 3-n-propyltoluene, 4-n-propyltoluene, and 1,3-diethylbenzene can also be present in the fluid.

In a hydrodealkylation process benzene, toluene, ethylbenzene and xylenes are generally substantially absent from the fluid, i.e., the amount of each of these aromatic hydrocarbons is less than about 0.1 weight % in the fluid. However, in a transalkylation process, one or more of benzene, toluene, ethylbenzene and xylenes can be present in the feed to effect a significant alkylation of the lower aromatic hydrocarbons by the $C_9+$ aromatic compounds, i.e., significant transalkylation occurs. The condition for carrying out hydrodealkylation and transalkylation can be substantially the same as disclosed hereinbelow.

Any hydrogen-containing fluid which comprises, consists essentially of, or consists of, molecular hydrogen ($H_2$) can be used in the process of this invention. This hydrogen-containing fluid can contain $H_2$ in the range of from about 1 to about 100, preferably about 5 to about 100, and most preferably 10 to 100 volume %. If the $H_2$ content in the fluid is less than 100%, the remainder of the fluid may be any inert gas such as, for example, $N_2$, He, Ne, Ar, steam, or combinations of any two or more thereof, or any other fluid which does not significantly affect the process or the catalyst composition used therein.

The contacting of a fluid feed stream containing a hydrocarbon with a hydrogen-containing fluid in the presence of the catalyst composition can be carried out in any technically suitable manner, in a batch or semicontinuous or continuous process, under a condition effective to convert a hydrocarbon to a $C_6$ to $C_8$, aromatic hydrocarbon. Generally, a fluid stream as disclosed above, preferably being in the vaporized state, is introduced into a suitable hydroprocessing reactor having a fixed catalyst bed, or a moving catalyst bed, or a fluidized catalyst bed, or combinations of any two or more thereof by any means known to one skilled in the art such as, for example, pressure, meter pump, and other similar means. Because a hydroprocessing reactor and process therewith are well known to one skilled in the art, the description of which is omitted herein for the interest of brevity. The condition of the process of the invention can include a weight hourly space velocity of the fluid feed stream in the range of about 0.01 to about 100, preferably about 0.05 to about 50, and most preferably 0.1 to 30 g feed/g catalyst/hour. The hydrogen-containing fluid (gas) hourly space velocity generally is in the range of about 1 to about 10,000, preferably about 5 to about 7,000, and most preferably 10 to 10,000 ft$^3$ H$_2$/ft$^3$ catalyst/hour. Generally, the pressure can be in the range of from about 10 to about 2000 psig, preferably about 100 to about 1000 psig, and most preferably 200 to 750 psig, and the temperature is about 250 to about 1000° C., preferably about 300 to about 750° C., and most preferably 400 to 650° C.

The process effluent generally contains a light gas fraction comprising hydrogen and methane; a $C_2$–$C_3$ fraction containing ethylene, propylene, ethane, and propane; an intermediate fraction including non-aromatic compounds having greater than 3 carbon atoms; a BTX aromatic hydrocarbons fraction (benzene, toluene, ortho-xylene, meta-xylene and para-xylene); and a $C_9$+fraction which contains aromatic compounds having 9 or more carbon atoms per molecule. Generally, the effluent can be separated into these principal fractions by any known methods such as, for example, fractionation distillation. Because the separation methods are well known to one skilled in the art, the description of which is omitted herein. The intermediate fraction can be fed to an aromatization reactor to be converted to aromatic hydrocarbons; methane, ethane, and propane can be used as fuel gas or as a feed for other reactions such as, for example, in a thermal cracking process to produce ethylene and propylene. The olefins can be recovered and further separated into individual olefins by any method known to one skilled in the art. The individual olefins can then be recovered and marketed. The BTX fraction can be further separated into individual $C_6$ to $C_8$ aromatic hydrocarbon fractions. Alternatively, the BTX fraction can further undergo one or more reactions either before or after separation to individual $C_6$ to $C_8$ hydrocarbons so as to increase the content of the most desired BTX aromatic hydrocarbon. Suitable examples of such subsequent $C_6$ to $C_8$ aromatic hydrocarbon conversions are disproportionation of toluene (to form benzene and xylenes), transalkylation of benzene and xylenes (to form toluene), and isomerization of meta-xylene and/or ortho-xylene to para-xylene.

After the catalyst composition has been deactivated by, for example, coke deposition or feed poisons, to an extent that the feed conversion and/or the selectivity to the desired ratios of olefins to BTX have become unsatisfactory, the catalyst composition can be reactivated by any means known to one skilled in the art such as, for example, calcining in air to burn off deposited coke and other carbonaceous materials, such as oligomers or polymers, preferably at a temperature of about 400 to about 1000° C. The optimal time periods of the calcining depend generally on the types and amounts of deactivating deposits on the catalyst composition and on the calcination temperatures. These optimal time periods can easily be determined by those possessing ordinary skills in the art and are omitted herein for the interest of brevity.

The following examples are presented to further illustrate this invention and are not to be construed as unduly limiting the scope of the present invention.

EXAMPLE I

This example illustrates the preparation of beta zeolite-containing compositions essentially according to the second embodiment of the invention.

Catalyst A was produced from a commercial Zeocat beta zeolite obtained from CU Utikon Chemie, Utikon, Switzerland. The beta zeolite (powder; 50 g) was well mixed with 50 g of CATAPAL® D alumina obtained from Vista Chemical Company (Houston, Texas), and 83 g of 10 weight % acetic acid followed by extrusion to produce an alumina-bound zeolite in 1/16 inch extrudates. The alumina-bound zeolite was calcined at 538° C. for 6 hours to produce catalyst A (alumina-bound zeolite). This was used as control.

This alumina-bound zeolite (catalyst A above; 3 g) was impregnated with a solution containing 2.07 g of 6.57 weight % ammonium molybdate ($(NH_4)_6Mo_7O_{24} \cdot 4H_2O$) by incipient wetness method at about 25° C. The ammonium molybdate-impregnated zeolite was then calcined in air (muffle furnace) for 6 hours at 538° C. to produce 2.93 g of molybdenum-promoted zeolite (catalyst B) containing 2.522 weight % molybdenum by calculation.

Catalyst C was prepared by first mixing 20 g of powder Zeocat beta zeolite with 400 g of aqueous solution of 1.0 M oxalic acid at 50° C. for 16 hours to produce a solid mixture. The mixture was then washed with running water for about 30 minutes at room temperature (about 25° C.) followed by drying at 125° C. for 16 hours to produce an acid-treated beta zeolite. The acid-treated beta zeolite was mixed with 20 g of CATAPAL® D alumina and 35 g of 10 weight % acetic acid to make a paste. The paste was extruded at 25° C. to 1/16 inch extrudates which were then calcined at 538° C. for 6 hours to produce 26.74 g of alumina-bound acid-treated beta zeolite. Of this 26.74 g, 3 g was impregnated with a solution containing 2.02 g of 6.57 weight % ammonium heptamolybdate ($(NH_4)_6Mo_7O_{24} \cdot 4H_2O$) solution by incipient wetness method followed by calcinating in air for 6 hours at about 538° C. to produce 2.96 g Mo-promoted acid-treated zeolite containing 2.409 weight % Mo by calculation.

EXAMPLE II

This example illustrates the use of the zeolite materials (catalysts A, B, and C) described in Example I in a transalkylation of a feed comprising $C_9$+ aromatic compounds and toluene to produce a product containing a higher concentration of BTX than the feed. The composition of aromatic compounds, up to 12 carbons per molecule, of the feed used for the transalkylation is shown in Table I. There were some paraffins, isoparaffins, and naphthenes as well as numerous unidentified components in the feed that are not shown in Table I.

TABLE I

| Aromatics (weight %) | $C_6$ | 0.000 |
|---|---|---|
| | $C_7$ (toluene) | 50.248 |
| | $C_8$ | 0.411 |
| | $C_9$ | 11.315 |
| | $C_{10}$ | 12.664 |
| | $C_{11}$ | 9.457 |
| | $C_{12}$ | 3.001 |
| | Total | 87.096 |
| Sulfur (ppmw) | | 658 |

A stainless-steel reactor tube (inner diameter: 2.5 cm; length: 50 cm) was filled with a 20 ml bottom layer of Alundum® alumina (inert, low surface area alumina, provided by Norton Company, Worcester, Mass.), 5 ml of one of the zeolite materials described in Example I, and a 20 ml top layer of Alundum®. The reactor and its content were pre-heated from room temperature to the desired reaction temperature of about 575° C. The zeolite-containing catalysts were pretreated with flowing hydrogen gas at a rate of 260 ml per minute at 500° C. starting at 25° C. and ramping at 10° C./min. The reaction pressure was set at 500 psig. A liquid feed as shown in Table I was introduced into the heated reactor at a rate of 20 ml/hour. The product, which exited the reactor, was cooled, analyzed by means of an online gas chromatograph at intervals of about 1 hour. The results are also summarized in Table II.

TABLE II

| Catal[a] | Time[b] (hr) | Temp (° C.) | % Conv $C_9$+ | % Conv[c] Naph | wt % Xyln's | wt % Lts[d] | Avg wt % Coke/hr[d] |
|---|---|---|---|---|---|---|---|
| A | 7.27 | 505 | 20.5 | 21.3 | 1.96 | 2.1 | 2.72 |
| B | 7.69 | 501 | 74.6 | 80.4 | 25.96 | 11.7 | 1.83 |
| C | 7.37 | 504 | 79.2 | 92.1 | 28.38 | 2.6 | 1.63 |

[a]See catalyst designations in Example I.
[b]Time of transalkylation or hydrodealkylation reaction.
[c]Conversion of naphthalenes.
[d]Light hydrocarbons having 6 or less carbona toms per molecule.
[e]Coke was determined at the end of the reaction by removing the catalysts from the reactor and determined with a thermal gravimetric analyzer (TGA), manufactured by TA Instruments, New Castle, Delaware.

The results shown in Table II demonstrate that use of a beta zeolite as catalyst (catalyst A) in transalkylation reaction had a low conversion of $C_9$+ aromatic compound. Impregnation of the zeolite with molybdenum (catalyst B) improved the conversion of $C_9$+ aromatic compounds to xylenes and reduced the coke rate in a transalkylation process as compared to the control (catalyst A), but significantly increased the low value hydrogenolysis products (lights: $C_1$–$C_6$). Table II also shows that an acid-treated beta zeolited impregnated with molybdenum (catalyst C) had considerably higher conversion of $C_9$+ aromatic compounds (including naphthalenes), higher xylenes yield, and lower coking rate than catalysts A and B.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

That which is claimed is:

1. A process for producing a zeolite composition consisting essentially of (1) contacting a beta zeolite with oxalic acid to produce an acid-treated beta zeolite; (2) contacting said acid-treated beta zeolite with a binder to provide a bound acid-treated beta zeolite (3) contacting said bound acid-treated beta zeolite with an activity promoter precursor selected from the group consisting of molybedenum compounds thereby incorporating said activity promoter precursor into said bound acid-treated beta zeolite to form a modified zeolite and (4) calcining said modified zeolite.

2. A process according to claim 1 wherein said molybdenum compounds are selected from the group consisting of molybdenum chlorides, molybdenum acetates, molybdenum fluorides, molybdenum hexacarbonyl, molybdenum sulfides, sodium molybdates, potassium molybdates, molybdenum oxychlorides, ammonium tetrathiomolybdate, ammonium molybdate, ammonium dimolybdate, ammonium heptamolybdate, and combinations of two or more thereof.

3. A process according to claim 2 wherein said molybdenum compound is ammonium heptamolybdate.

4. A process according to claim 1 wherein the weight ratio of said zeolite to said binder is in the range of from about 200:1 to about 0.1:1.

5. A processing according to claim 4 wherein said contacting step (1) is conducted under conditions comprising a concentration of said beta zeolite in an oxalic acid solution in the range of from about 0.01 to about 500 grams per liter; an initial pH of said oxalic acid solution adjusted to lower than about 7; a temperature in the range of from about 30° C. to about 200° C.; a time period in the range of from about 10 minutes to about 30 hours; and a pressure in the range of from about 1 to about 10 atmospheres.

6. A process according to claim 5 wherein said acid-treated beta zeolite is dried and calcined.

7. A process for producing a zeolite composition consisting essentially of (1) contacting a beta zeolite with oxalic acid to produce an acid-treated beta zeolite; (2) contacting said acid-treated beta zeolite with a binder to provide a bound acid-treated beta zeolite (3) contacting said bound acid-treated beta zeolite with an activity promoter precursor consisting essentially of ammoniumheptamolybdate thereby incorporating said activity promoter precursor into said bound acid-treated beta zeolite to form a modified zeolite and (4) calcining said modified zeolite.

* * * * *